United States Patent
Beck

(10) Patent No.: US 9,174,915 B2
(45) Date of Patent: Nov. 3, 2015

(54) EXTRACTION TOWERS AND PROCESSES FOR USING THE SAME

(75) Inventor: Carl R. Beck, Baton Rouge, LA (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 160 days.

(21) Appl. No.: 13/695,757

(22) PCT Filed: May 4, 2011

(86) PCT No.: PCT/EP2011/057090
§ 371 (c)(1),
(2), (4) Date: Feb. 13, 2013

(87) PCT Pub. No.: WO2011/151123
PCT Pub. Date: Dec. 8, 2011

(65) Prior Publication Data
US 2013/0204023 A1 Aug. 8, 2013

Related U.S. Application Data

(60) Provisional application No. 61/351,572, filed on Jun. 4, 2010.

(30) Foreign Application Priority Data

Jul. 16, 2010 (EP) .................................. 10169784

(51) Int. Cl.
| C07C 51/48 | (2006.01) |
| B01D 11/04 | (2006.01) |
| C07C 53/128 | (2006.01) |

(52) U.S. Cl.
CPC ............... *C07C 51/48* (2013.01); *B01D 11/04* (2013.01); *C07C 53/128* (2013.01)

(58) Field of Classification Search
CPC ....... C07C 51/48; C07C 53/128; B01D 11/04
See application file for complete search history.

(56) References Cited

U.S. PATENT DOCUMENTS

| 3,061,621 A | 10/1962 | Koch et al. |
| 3,068,256 A | 12/1962 | Roming |
| 3,349,107 A | 10/1967 | Pawlenko |
| 3,527,779 A | 9/1970 | Paulis et al. |
| 3,609,185 A * | 9/1971 | Yeomans et al. ............... 562/521 |

(Continued)

FOREIGN PATENT DOCUMENTS

| CN | 101081811 | 12/2007 |
| EP | 0 298 431 | 4/1994 |

(Continued)

OTHER PUBLICATIONS

Scheibel, E.G., Performance of and Internally Baffled Multistage Extractin Column, 1956, A.I.Ch.E. Journal, vol. 2, No. 1, pp. 74-78.*

(Continued)

*Primary Examiner* — Yate K Cutliff
(74) *Attorney, Agent, or Firm* — Leandro Arechederra, III; Luke A. Parsons

(57) ABSTRACT

The disclosure relates to processes and systems utilizing one or more extraction towers in the recovery and recycle of acid catalysts used in the production of carboxylic acids. The carboxylic acids may be neo-acids produced through the hydrocarboxylation of olefins or olefin mixtures.

15 Claims, 4 Drawing Sheets

(56) References Cited

U.S. PATENT DOCUMENTS

| | | | |
|---|---|---|---|
| 3,910,963 A | 10/1975 | Souma et al. | |
| 4,169,809 A * | 10/1979 | Pugach | 423/112 |
| 4,256,913 A | 3/1981 | Jung et al. | |
| 4,311,851 A | 1/1982 | Jung et al. | |
| 4,518,798 A | 5/1985 | Kramer et al. | |
| 4,761,505 A * | 8/1988 | Diana et al. | 568/918 |
| 5,223,641 A * | 6/1993 | Kawasaki et al. | 562/521 |
| 5,241,112 A | 8/1993 | Sanderson et al. | |
| 6,211,406 B1 * | 4/2001 | Lange et al. | 562/521 |
| 6,677,481 B2 | 1/2004 | Mozeleski et al. | |
| 6,717,010 B2 | 4/2004 | Mozeleski et al. | |
| 6,881,859 B2 | 4/2005 | Mozeleski et al. | |
| 6,919,474 B2 | 7/2005 | Mozeleski et al. | |
| 2005/0197507 A1 | 9/2005 | Wiese et al. | |

FOREIGN PATENT DOCUMENTS

| | | |
|---|---|---|
| EP | 0 590 087 | 1/1997 |
| GB | 1 167 116 | 10/1969 |
| GB | 1 174 209 | 12/1969 |
| JP | 2005-154298 | 6/2005 |
| WO | WO 2009/091491 | 7/2009 |
| WO | WO 2009/130386 | 10/2009 |
| WO | WO 2011/151123 | 12/2011 |

OTHER PUBLICATIONS

Johnson et al., *Carboxylic Acids, Trialkylacetic Acids,* Kirk-Othmer Encyclopedia of Chemical Technology Fourth Ed., vol. 5, pp. 1-14.

Ellis et al., "*Make Low-Cost Carboxylic Acids From Olefins, Carbon Monoxide and Water,*" Hydrocarbon Processing, vol. 44, No. 6, pp. 139-141, Jun. 1965.

* cited by examiner

EXTRACTION TOWERS AND PROCESSES FOR USING THE SAME

CROSS REFERENCE TO RELATED APPLICATIONS

This application is a National Stage Application of International Application No. PCT/EP2011/057090, filed May 4, 2011, which claims the benefit of Ser. No. 61/351,572 filed Jun. 4, 2010, and EP 10169784.5, filed Jul. 16, 2010, the disclosures of which are incorporated herein by reference in their entireties.

FIELD OF THE INVENTION

Embodiments described herein generally relate to processes and systems utilizing one or more extraction towers in the recovery and recycle of acid catalysts used in the production of carboxylic acids. The carboxylic acids may be neo-acids produced through the hydrocarboxylation of olefins or olefin mixtures.

BACKGROUND

Neo-acids, including trialkylacetic acids, are generally carboxylic acids having at least one carboxyl group and at least one carbon connected directly to four other carbon atoms. Salts and other derivatives of neo-acids generally are very stable due primarily to the steric hindrance provided by their molecular structure. In particular, the alkyl groups on the alpha substituted carbon atom create a steric effect and hinder the ability of the neo-acid or its derivative to react. As a result, neo-acids or their derivatives have broad industrial applications, such as, for example, polymers and polymer additives, pharmaceuticals, agricultural chemicals and herbicides/pesticides, cosmetics, metal working and metal extraction fluids, vinyl chemical manufacturing, catalysts carriers and catalyst additives, aroma chemicals, fuels, lubricants, adhesives, transmission fluids, hydraulic fluids, tire manufacturing, electrical and electronic applications, etc. Common derivatives of neo-acids include acid chlorides, peroxyesters, metal salts, vinyl esters, and glycidyl esters.

Two industrial processes have been used to produce neo-acids on a large commercial scale. The first is commonly referred to as Shell's versatic acid process and the second as the Exxon process. Schematics and descriptions of each production process may be found in *Carboxylic Acids (Trialkylacetic Acids)*, Johnson et al., Kirk-Othmer Encyclopedia of Chemical Technology Fourth Ed., Vol. No. 5, pages 192-206. In particular, the Exxon process may generally include reaction, degassing, catalyst recovery, and fractionation. Both processes use, as starting materials, olefins, carbon monoxide (CO), and acid catalysts in continuous stirred tank reactors to produce carboxylic acids. Typical reactions conditions include 40 to 100° C. and 70 to 100 bar carbon monoxide pressure with $H_3PO_4/BF_3/H_2O$ in the ratio of 1:1:1 (Shell) or $BF_3 \cdot 2H_2O$ (Exxon).

Background references include U.S. Pat. Nos. 3,061,621; 3,068,256; 3,349,107; 3,527,779; 4,256,913; 4,311,851; 4,518,798; 5,241,112; 6,677,481; 6,717,010; 6,881,859; 6,919,474; U.S. Patent Application Publication No. 2005/0197507; GB 1,167,116; GB 1,174,209; and EP 0 590 087 B.

Due to the catalysts employed, a series of washing steps and settling drums are generally used primarily to recover and recycle catalyst and secondarily to remove metals and other catalysts components, such as, for example, residual salts and corrosion byproducts, from the crude carboxylic acid reactor effluent. Despite satisfactory approaches of the past, improvements in the removal of these materials remain highly desirable.

SUMMARY

In a class of embodiments, the invention provides for a process comprising: obtaining a reactor effluent from one or more reactors comprising a mixture of one or more of at least one neo-acid, at least one catalyst, at least one catalyst salt, at least one complex of at least one catalyst and at least one neo-acid, and mixtures thereof; passing the reactor effluent through at least one extraction tower; contacting at least a portion of the mixture with water; separating at least a portion of the neo-acid from the mixture to form at least one separated neo-acid; and recovering the at least one separated neo-acid; wherein the at least one extraction tower comprises two or more phases operating at least two extractions.

In another class of embodiments, the invention provides for a system comprising: (a) at least one reactor for the production of at least one neo-acid; and (b) at least one extraction tower comprising two or more phases operating at least two extractions.

Embodiments including variations of the aforementioned process and system are also disclosed and claimed herein.

DETAILED DESCRIPTION

Figure 1:
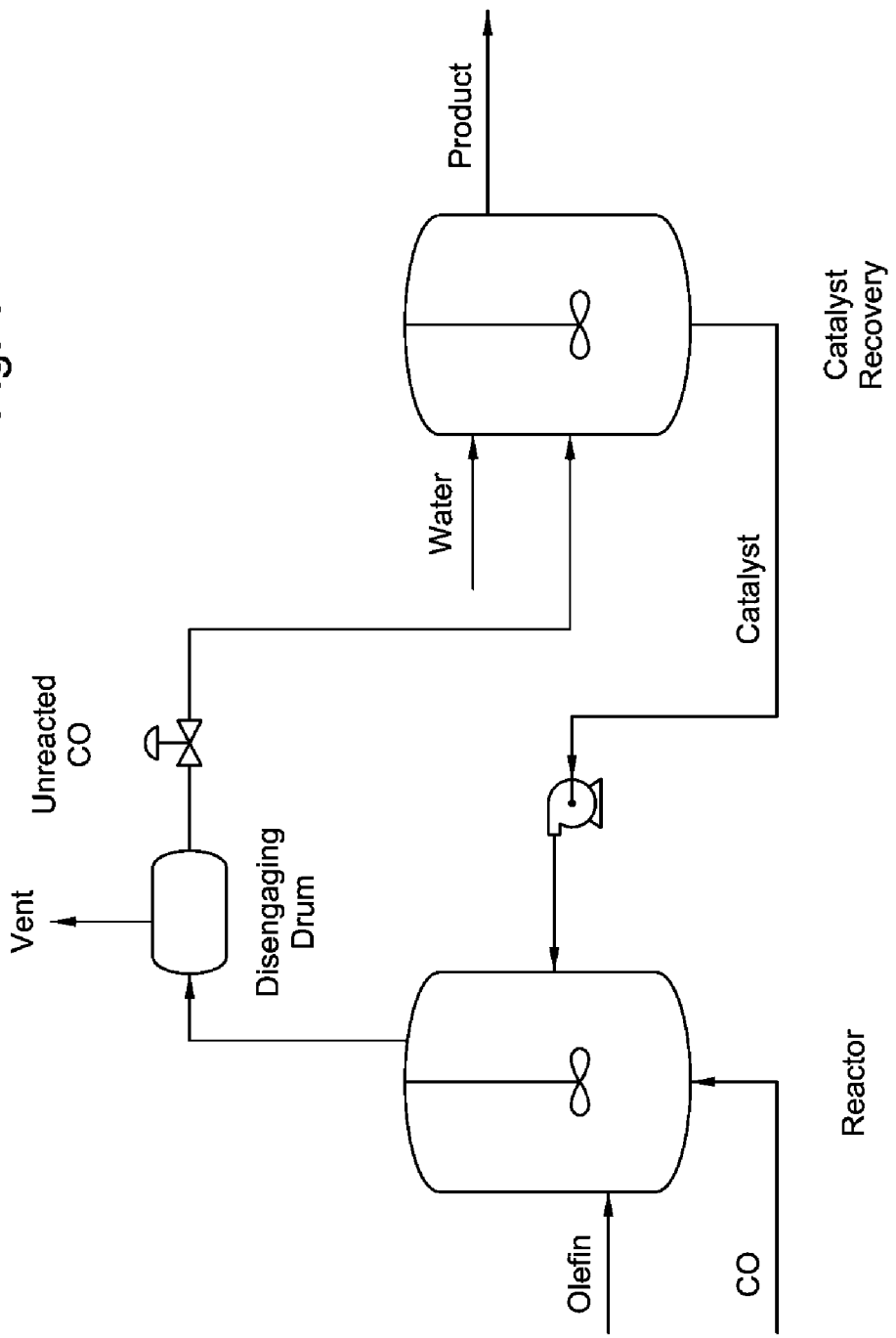
FIG. 1 is a simplified flow diagram directed to the preparation of neo-acids.

Before the present compounds, components, compositions, devices, equipment, configurations, schematics, systems, and/or methods are disclosed and described, it is to be understood that unless otherwise indicated this invention is not limited to specific compounds, components, compositions, devices, equipment, configurations, schematics, systems, methods, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an" and "the" include plural referents unless otherwise specified.

Carboxylic Acid Production

Carboxylic acids including, for example, neo-acids and versatic acids may be produced by any suitable process and reactor system known in the art in accordance with embodiments described herein. For example, carboxylic acids, such as, for example, mono-carboxylic acids, may be prepared from olefin starting materials (including mixed olefin feeds, i.e., olefins having different carbon numbers, and/or olefin feeds comprising isomers) utilizing Koch synthesis by the carbonylation of olefins with carbon monoxide in the presence of strong acid catalysts, for example, Bronsted acid catalysts (e.g., $H_2SO_4$, $H_3PO_4$, HF, etc.), and/or Lewis acid catalysts (e.g., $BF_3$, etc.) to form a carbenium ion from the olefin, then followed by the addition of CO and water (or, in some embodiments, alcohol) to form the carboxylic acid (or, in some embodiments, ester), such as the neo-acid(s) or a random mixture isomeric neo-acids. A particularly useful process has been developed for the carbonylation of olefins utilizing boron trifluoride dihydrate as the acid catalyst as described in, for example, "Hydrocarbon Processing", 44, 139 (1965). In particular and in an embodiment, 2,2-dimethyl propionic acid (also known as neo pentanoic acid) is prepared using a Koch synthesis by reacting isobutylene and carbon monoxide in the presence of $BF_3.2H_2O$ to produce a neo-acid. Neo-acid as used herein refers to carboxylic acids having at least one carboxyl group and the adjacent (alpha) carbon connected directly to four other carbon atoms, or, alternatively stated, a tetra substituted alpha carbon. Examples include pivalic acid, neo-$C_9$ carboxylic acid, neo-$C_{13}$ carboxylic acid, neoheptanoic acid, neodecanoic acid, etc.

In a class of embodiments, useful neo-acids include carboxylic acids have a carbon number from $C_5$ to $C_{13}$. Neo-acid may also refer to any trialkylacetic acid. The trialkylacetic acid may be represented by the following formula:

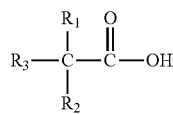

Formula I wherein each $R_1$, $R_2$, and $R_3$ may be independently $C_xH_{2x+1}$, with $x \geq 1$. In a class of embodiments, x is from 1 to 12, preferably, from 1 to 9.

Other exemplary and useful disclosures may be found in, for example, U.S. Pat. Nos. 3,061,621; 3,068,256; 3,349,107; 3,527,779; 4,256,913; 4,311,851; 4,518,798; 5,241,112; 6,677,481; 6,717,010; 6,881,859; 6,919,474; U.S. Patent Application Publication No. 2005/0197507; GB 1,167,116; GB 1,174,209; and EP 0 590 087 B.

In these reactions, an acid with a carbon number one higher than the starting feed olefin is produced. Starting materials may include isobutylene for neo-pentanoic (C5) acid and branched nonenes for neo-decanoic (C10) acid. Other materials may be used such as, for example, hexenes for (C7) acid or tetrapropylene for (C13) acid. The reaction sequence generally includes carbonylation of the olefin into an acid complex with an acid catalyst and then water addition to separate the carboxylic acid from the catalyst.

Most widely used Koch processes include a boron trifluoride catalyst system containing water and sometimes a co-catalyst such as phosphoric acid or sulfuric acid. When such a co-catalyst is used, it may generally be present at a molar ratio of from about 0.1 to about 1 mole per mole of boron trifluoride catalyst. The process requires the regeneration or recovery of the catalyst in a step in which the amount of water added is critical to the efficiency of the process. Other catalysts may be used such as, for example, $BF_3$ (gas), $BF_3.H_2O$, $H_3PO_4$, $H_2SO_4$, HF, and mixtures thereof. In some embodiments, they may be used with co-catalysts, for example, $Cu^+$ or $Ag^+$. However, it is contemplated that any strong acid should be useful with embodiments described herein.

A schematic of an exemplary neo-acid production process is shown in FIG. 1. In general, synthesis gas containing CO and hydrogen is concentrated by removing hydrogen via permeation, adsorption, or cryogenic processes. The feed olefin(s), catalyst(s), and concentrated CO are then fed to a continuous well-mixed reactor where the olefin reacts at high pressure and low temperature. Water is added to the reactor effluent to wash the carboxylic acid product and release catalyst as a separate phase which is then separated and recycled. The product acid may subsequently be distilled to remove light and heavy acids.

In a class of embodiments, the catalyst is at least one selected from the group consisting of: alcohols of boron trifluoride, including $BF_3xCH_3OH$, $BF_3xC_2H_5OH$, $BF_3xC_3H_8OH$, and mixtures thereof, wherein x may be from about 2.0 to 2.5.

In another class of embodiments, $BF_3.2H_2O$ is a useful catalyst for the production of neo-acids. For example, one of the advantages associated with the use of $BF_3.2H_2O$ as a catalyst in such processes is that it is very active in the reaction sequence for producing neo-acids and that it may be readily regenerated for recycle in the system from the complex formed between $BF_3.2H_2O$, the olefin, and carbon monoxide reactants by careful control of the amount of water entering the catalyst recovery section. Control of the amount of water introduced determines whether the desired catalyst is regenerated with an optimum $H_2O$ to $BF_3$ ratio.

For processes that lend themselves to the recovery, regeneration, and recycle of the catalyst, embodiments disclosed herein may include the use of one or more extraction towers. As such, these processes provide substantial commercial advantages for the obvious benefits associated with recycling of the catalyst and obtaining a concentrated or purified finished product that is free or substantially free of the catalysts, catalyst components, catalyst salts, and/or corrosion byproducts. As used herein, "catalysts and/or catalyst salts" refers to the anions, $^-BF_4$ and $^-BF_2(OH)_2$, as well as $^-BF_3OH$. Although undesirable, boric acid can also be formed under less than ideal conditions. The anion $^-BF(OH)_3$ is rarely present. In some embodiments, "substantially free" refers to a ppm level of 25 ppm or less, alternatively, 5 ppm or less, alternatively, 1 ppm or less, and alternatively, 0.1 ppm or less of the catalysts and/or catalyst salts. Additionally, in some embodiments, the anions described above can exist as acids or salts with the metals described below. As used herein, "corrosion byproducts" refers to the metal salts of the materials and/or equipment of construction and manufacture. For example, if stainless steel were the material of construction, oxides and salts of the metals, iron, chromium, nickel, molybdenum, manganese, along with the ubiquitous sodium and silica would be expected as the acid catalysts are corrosive.

Extraction Tower and Extraction Tower Operation

Figure 2:
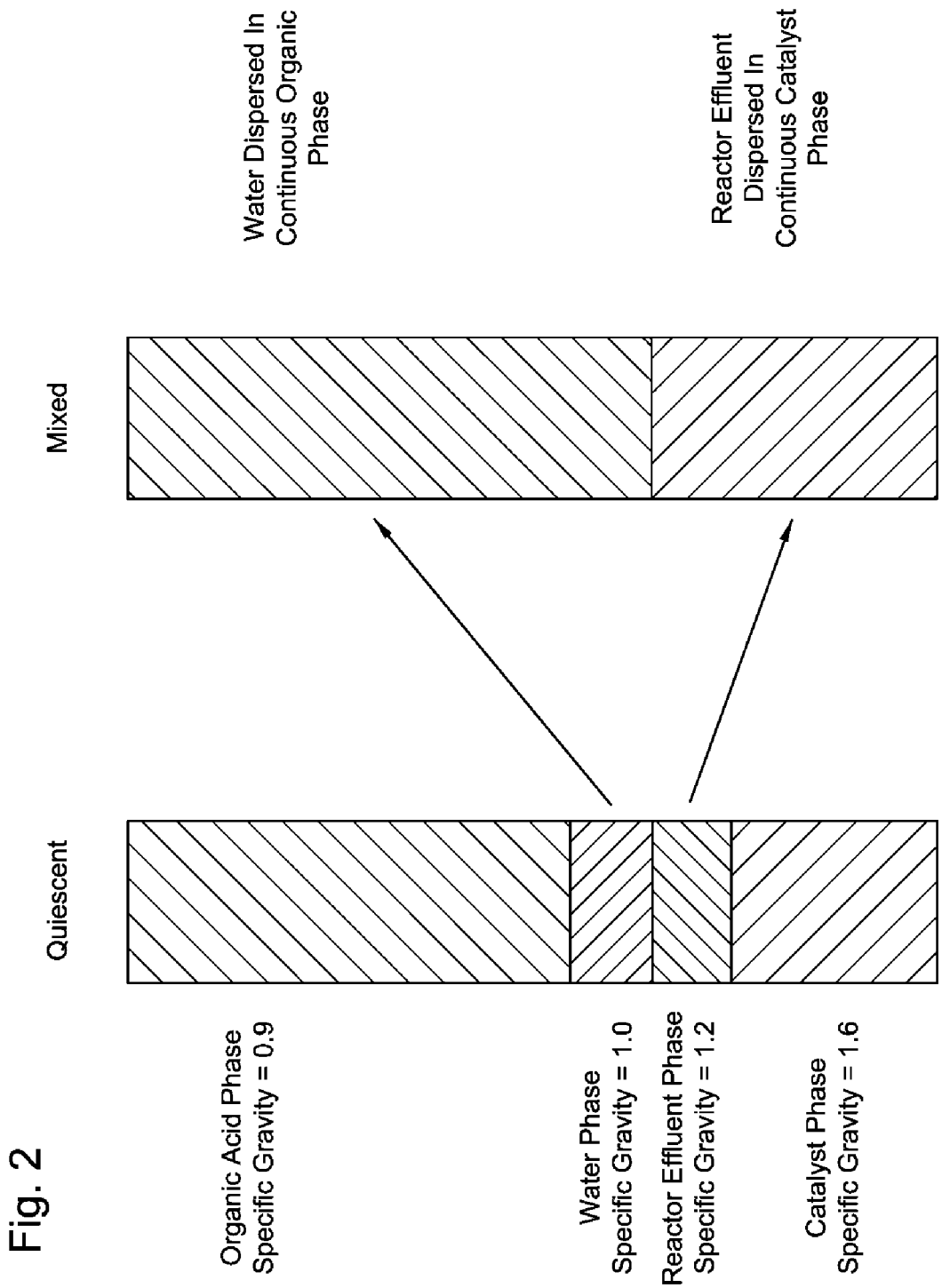
FIG. 2 is an example of an extraction tower showing various phases in both quiescent and mixed environments.

In several classes of embodiments, the process of using water to recover catalyst creates two or more liquid phases and in other embodiments four or more liquid phases. The number of phases may depend upon whether a tower is in quiescent or mixing (mixed) mode as represented in FIG. 2. The product carboxylic acid is highly organic and has a lower density than water. The reactor effluent which is primarily the product carboxylic acid complexed with catalyst is highly organic in nature and is thus immiscible in the heavier inorganic catalyst phase as represented in FIG. 2. It is important to avoid adding excess water to the catalyst phase as this dilution would render the catalyst inactive for reaction by irreversibly forming boric acid. In several embodiments, water is added only to the carboxylic acid-catalyst complex. Thus, in these embodiments, it is efficient to add water to the reactor effluent stream in a counter current fashion or by counter current extractions.

Due to the inorganic and corrosive nature of the catalyst, it may contain many inorganic salts that are capable of catalyzing unwanted side reactions. These salts may be removed by water washing the organic carboxylic product. Again for the purpose of efficiency, the same water added to wash the product may be used for catalyst recovery and thereby return catalyst salts extracted from the product back into the catalyst stream that improves catalyst recovery and leaves a product that is surprisingly low in color. This double process step (washing and catalyst recovery) may be accomplished with large mixing and settling drums as applied in the art or with much greater efficiency with mechanical extraction towers as included in several embodiments disclosed herein. One or more extraction towers may be included in the catalyst recovery and recycle process. Tower is sometimes used synonymously with column as recognized in the art. Suitable towers include York-Scheibel towers. Such towers are generally devices that contain alternating mixing and settling stages in a tower configuration. They are commonly used for the extraction of solutes from one liquid phase to another liquid phase. However, they may be configured to act as a multiple phase, for example, two or more phase, tower operating two liquid/liquid extractions, stacked on top of one another in several embodiments disclosed herein. The towers have been described, for example, in *Performance of an Internally Baffled Multistage Extraction Column*, Scheibel, Edward G., A. I. Ch. E. Journal, March, 1956, pages 74-78.

In a class of embodiments, in the top section (for example, the top (⅔) section of the tower), water is the dispersed phase falling through the continuous phase of crude neo-acid which is flowing upward. In a class of embodiments, the top section is from 40% to 75% of the at least one extraction tower and the bottom section is from 60% to 25% of the at least one extraction tower. As the water falls through, inorganic residual salts of catalyst and corrosion byproducts are extracted from the rising crude acid. A liquid/liquid interface defines the bottom of this upper section. In an embodiment, the use of the York-Scheibel tower for this purpose increases the efficiency of extraction by allowing from 10 to 75, alternatively, from 20 to 40, alternating mixing and settling stages. The mixing stages create very small droplet sizes with excellent mass transfer for extraction. In addition, the efficient mixing action keeps the water dispersed and thereby reduces the possibility of a large quantity of water eventually contacting catalyst which tends to initiate unwanted reactions. In the case of the catalyst $BF_3.H_2O$, high water concentrations will encourage the irreversible reaction to boric acid rendering the catalyst useless.

Below this interface, the bottom section (for example, the bottom ⅓ section of the tower) consists of a continuous phase of catalyst that may be described by the following:

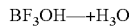

$$BF_3OH^-+H_3O^+$$

and a lighter dispersed phase of the reactor effluent (herein "complex") which is a fluoroborate salt of the protonated carboxylic acid that may be described by the following:

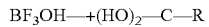

$$BF_3OH^-+(HO)_2-C-R$$

wherein R is a hydrocarbon group from 4 to 12.

As used herein, "hydrocarbon" refers to molecules or groups of molecules containing all or primarily hydrogen and carbon atoms.

Water which is dispersed and falling through the upper phase readily crosses the interface referenced above and reacts with the complex dispersed in the lower, catalyst phase that may be described by the following:

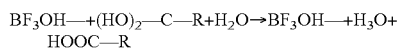

$$BF_3OH^-+(HO)_2-C-R+H_2O \rightarrow BF_3OH^-+H_3O^+ + HOOC-R$$

wherein R is a hydrocarbon group from 4 to 12.

This reaction frees the neo-acid from the complex and the neo-acid rises as it is lighter than the catalyst, crosses the interface, and continues rising through the upper section of the tower, exiting as the overhead product. The heavier catalyst (for example, $BF_3.2H_2O$) falls through the bottom section of the tower and is removed as a bottom stream.

In several embodiments, it is important that a precise amount of water must be added to the tower, for example, at the top of the tower. Too much water will readily go into the catalyst, lowering the catalyst acidity, and degrade reaction selectivity. Insufficient water will force an excessive amount of complex out of the bottom of the tower. Taken to an extreme deficiency of water, the interface will become unsustainable. In an embodiment, water addition may be the molar equivalent of the amount of carboxylic acid that is produced in the reactor as this water is replacing the water that was consumed in the formation of the carboxylic acid.

Figure 3:
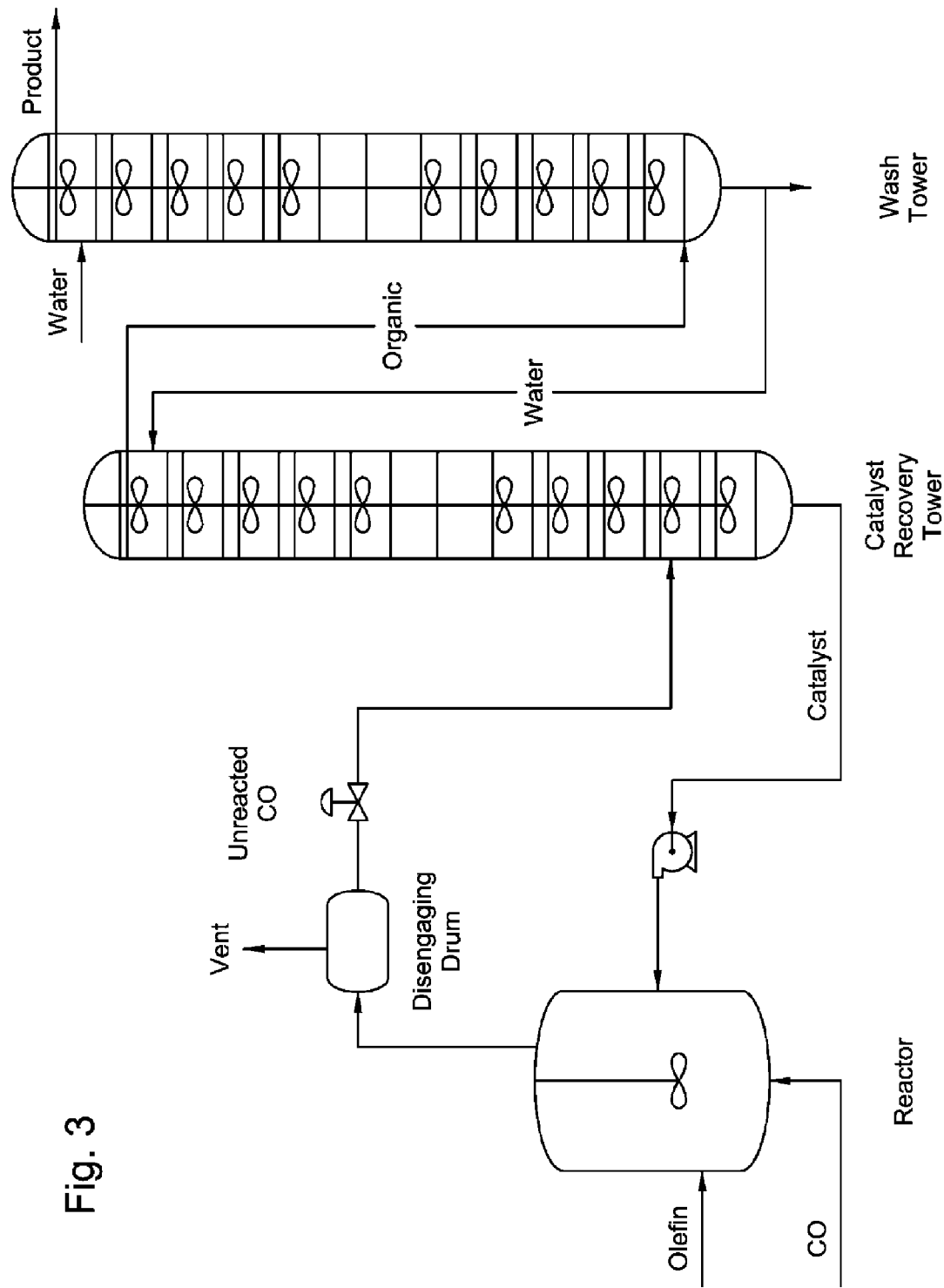
FIG. 3 is a representation of a two tower configuration design for neo-acid production including catalyst recovery and recycle.

In a class of embodiments, a two process steps, catalyst recovery and product washing can be accomplished with two towers, separating the two steps as shown in FIG. 3. An advantage of this configuration is that the amount of water added to the wash section is not limited to a stoichiometric amount equal to carboxylic acid.

Figure 4:
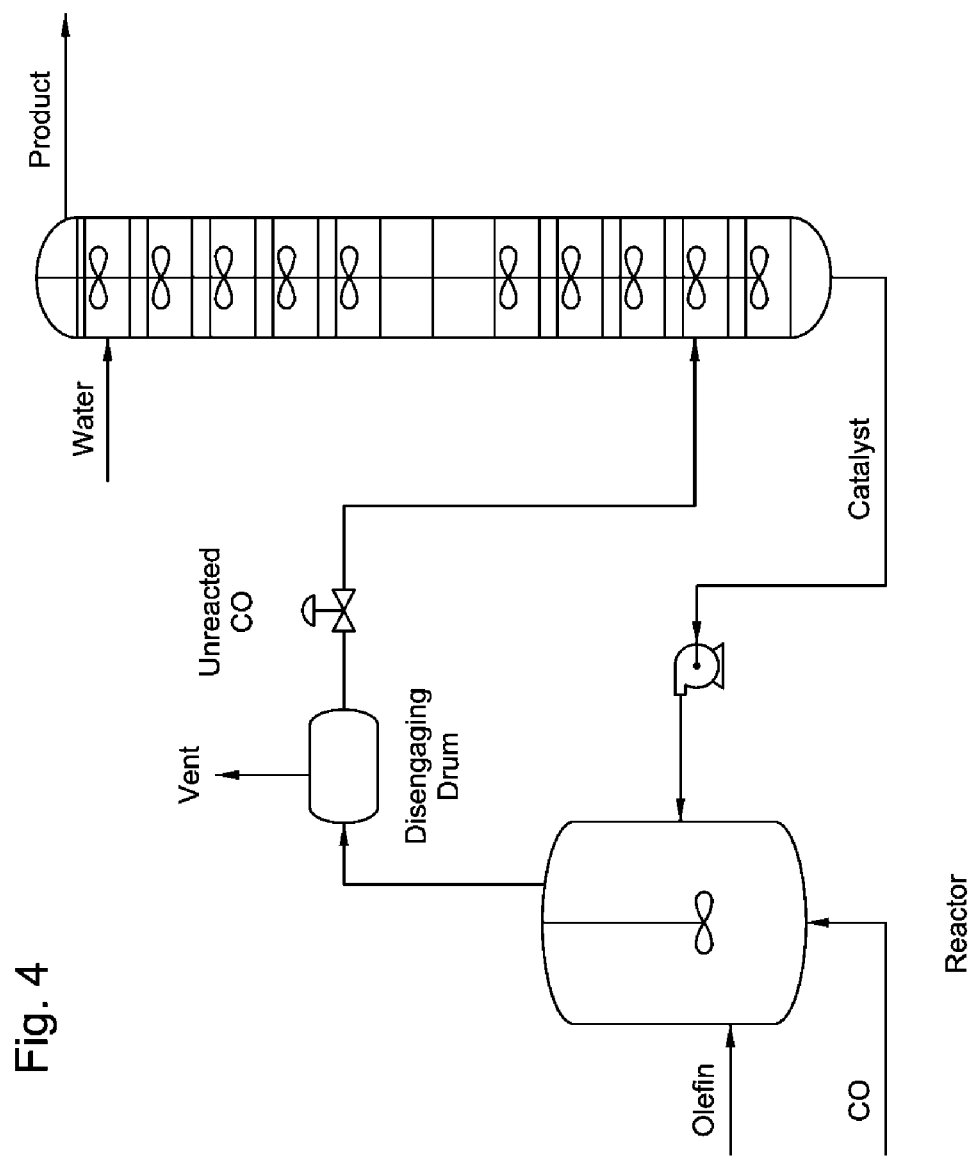
FIG. 4 is a representation of a one tower configuration design for neo-acid production including catalyst recovery and recycle.

In another class of embodiments, dual extraction may be accomplished in only one tower as shown in FIG. 4. Dual extraction in a single process vessel gives excellent removal of catalyst salts (in the <10 ppm range) as well as excellent catalyst recovery and control of catalyst strength.

In any of the embodiments described herein, the separated at least one neo-acid may have 20 ppm or less of the catalysts and/or catalyst salts, alternatively, 10 ppm or less of the catalysts and/or catalyst salts, alternatively, 5 ppm or less of the catalysts and/or catalyst salts, alternatively, 1 ppm or less of the catalysts and/or catalyst salts, and alternatively, .1 ppm or less of the catalysts and/or catalyst salts.

The treated product exiting the catalyst recovery tower(s) described above is free or substantially free of inorganic contaminants, and yet saturated with water. This product has been found to be surprisingly low in color.

In some embodiments, a downstream wash tower can be employed to remove inorganic contaminants in case of an upset. An additional water stripping step or heart cut distillation can be used to produce a dry or narrow carbon range product if desired.

Industrial Application

Neo-acids and their derivatives have broad industrial applications, such as, for example, polymers and polymer additives, pharmaceuticals, agricultural chemicals and herbicides/pesticides, cosmetics, metal working and metal extraction fluids, vinyl chemical manufacturing, catalysts carriers and catalyst additives, fuels, lubricants, adhesives and adhesion promoters, aroma chemicals, transmission fluids, hydraulic fluids, tire manufacturing, electrical and electronic applications, etc.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the invention, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All priority documents are herein fully incorporated by reference for all jurisdictions in which such incorporation is permitted and to the extent such disclosure is consistent with the description of the present invention. Further, all documents and references cited herein, including testing procedures, publications, patents, journal articles, etc., are herein fully incorporated by reference for all jurisdictions in which such incorporation is permitted and to the extent such disclosure is consistent with the description of the present invention.

While the invention has been described with respect to a number of embodiments and examples, those skilled in the art, having benefit of this disclosure, will appreciate that other embodiments can be devised which do not depart from the scope and spirit of the invention as disclosed herein.

What is claimed is:

1. A process comprising:
   producing in one or more reactors at least one neo-acid by carbonylation of olefins utilizing a boron trifluoride catalyst system containing water thereby obtaining a reactor effluent from said one or more reactors comprising a mixture of a neo-acid, and one or more of a catalyst, a catalyst salt, and a complex of a catalyst and a neo-acid;
   passing the reactor effluent through at least one extraction tower;
   contacting at least a portion of the reactor effluent with water;
   separating at least a portion of the neo-acid from the reactor effluent; and
   recovering the separated neo-acid;
   wherein the at least one extraction tower comprises two or more phases operating at least two extractions.

2. The process of claim 1, wherein the at least two extractions are liquid/liquid extractions and the at least one extraction tower comprises two or more phases in mixing mode or four or more phases in quiescent mode.

3. The process of claim 1, wherein the at least one extraction tower is a York-Scheibel tower.

4. The process of claim 1, wherein the at least one tower comprises from 20 to 40 alternating mixing and settling stages.

5. The process of claim 1, wherein the at least one tower comprises water and the water concentration is the molar equivalent to the at least one neo-acid from the reactor effluent.

6. The process of claim 1, wherein the process further comprises utilizing a second extraction tower; wherein the second extraction tower comprises water and the water concentration is not the molar equivalent to the at least one neo-acid from the reactor effluent.

7. The process of claim 1, wherein at least a portion of the catalyst is recycled to the one or more reactors.

8. The process of claim 1, wherein the at least one extraction tower comprises a top section, a bottom section, and an interface.

9. The process of claim 8, wherein the top section is from 40% to 75% of the at least one extraction tower and the bottom section is from 60% to 25% of the at least one extraction tower.

10. The process of claim 8, wherein the interface is a liquid/liquid interface.

11. The process of claim 1, wherein the reactor effluent is a reactor effluent derived from contact with the boron trifluoride catalyst system and wherein a catalyst of the system is selected from the group consisting of $H_3PO_4/BF_3/H_2O$, $BF_3 \cdot 2H_2O$, and mixtures thereof.

12. The process of claim 11, wherein the reactor effluent is a reactor effluent derived from contact with $BF_3 \cdot 2H_2O$.

13. The process of claim 8, wherein the top section comprises a dispersed phase of water and a continuous phase of the at least one neo-acid from the reactor effluent, wherein the bottom section comprises a dispersed phase of fluoroborate-carboxylic acid salt represented by the formula $BF_3OH$—$^+$ $(HO)_2$—C—R and a continuous phase of a catalyst represented by the formula $BF_3OH$—$+^+H_3O$, wherein R is a hydrocarbon group from 4 to 12, to form the at least one separated neo-acid.

14. The process of claim 1, wherein the at least one separated neo-acid is represented by the formula:

$$\underset{R_2}{\overset{R_1}{R_3-C-}}\overset{O}{\overset{\|}{C}}-OH \qquad \text{Formula I}$$

wherein each $R_1$, $R_2$, and $R_3$ may be independently $C_xH_{2x+1}$, and x is from 1 to 12.

15. The process of claim 1, wherein the at least two extractions are counter current extractions.

* * * * *